United States Patent [19]

Ong et al.

[11] 4,269,057
[45] May 26, 1981

[54] MULTIPURPOSE HUMIDITY CONTROLLED AGENT GENERATOR

[75] Inventors: Kwok Y. Ong, Aberdeen; Michael T. Packard, Bel Air; Charles J. McDowell, Edgewood, all of Md.

[73] Assignee: The United States of America as represented by the Secretary of the Army, Washington, D.C.

[21] Appl. No.: 87,892

[22] Filed: Oct. 24, 1979

[51] Int. Cl.³ ............................................. G01N 31/00
[52] U.S. Cl. .................................. 73/1 G; 23/232 R; 422/83
[58] Field of Search ................... 73/1 G; 23/232 R; 422/83, 98

[56] References Cited

U.S. PATENT DOCUMENTS

| 3,665,748 | 5/1972 | Mator | 73/1 G |
| 4,069,701 | 1/1978 | Baldauf et al. | 73/1 G |

*Primary Examiner*—James J. Gill
*Attorney, Agent, or Firm*—Nathan Edelberg; Robert P. Gibson

[57] ABSTRACT

A test agent generator system capable of producing a controlled concentration of chemical agent vapors and aerosols under variable, controlled temperature and relative humidity conditions for use in a method of calibrating and testing agent sensitivity of a point-source alarm system.

23 Claims, 1 Drawing Figure

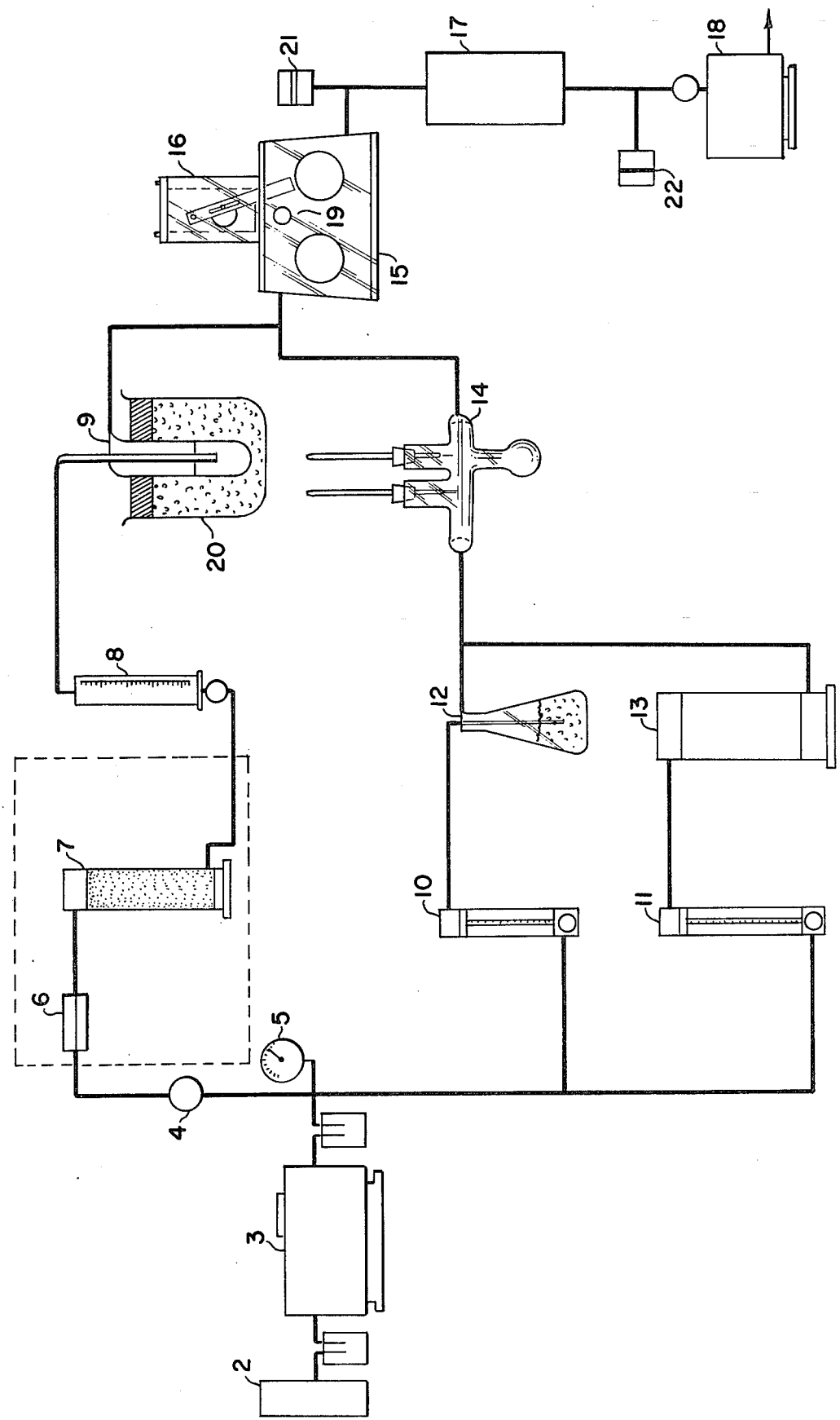

MULTIPURPOSE HUMIDITY CONTROLLED AGENT GENERATOR

DEDICATORY CLAUSE

The invention described herein may be manufactured, used, and licensed by or for the Government for governmental purposes without the payment to us of any royalty thereon.

BACKGROUND OF THE INVENTION

The invention relates to a test agent generation system for producing a constant concentration of test agent vapor or aerosol at controlled condition of temperature and relative humidity for use in calibrating and testing the agent, e.g., the toxic agents HD, GB and VX and other chemical vapors and aerosols, sensitivity of point source alarm systems.

The invention also relates to a vapor and aerosol dilution apparatus which can provide varied and controlled temperature and humidity conditions of agent for testing the performance of detection apparatus under simulated atmospheric conditions of temperature and relative humidity paralleling expected operational environments.

The problem of reliably determining the minimum agent detection capability of various toxic chemical vapor and aerosol detectors, e.g., a point source detection system, under field operational conditions has long existed in the art.

Several prior art methods have been used for determining the toxic agent detection capability of an alarm in the field. Quinine sulfate solutions, for example, have been introduced into the cell of point source agent alarms to check the optical and electrical systems. These solutions do not, however, check the alarm systems capability to sample the atmosphere, extract suspected agent from the air and chemically react the agent with the alarm system.

Various devices containing the actual agent under static conditions, either in solution or in an absorbent material, have been used to provide a test vapor, but have not been proven to be reliable for producing the constant vapor of agent required for use in determining the detection concentration capability of the alarm in the field. The vapor output from these devices is changeable to a degree from changes in air temperature. In addition, the generator vapor, when not in use, is contained under static conditions and consequently, the vapor eluted under dynamic conditions could not be at equilibrium.

A laboratory method of generation, low, constant and reliable concentrations of agent is with a glass vapor dilution apparatus containing agent in a pure form. This apparatus requires at least 24 hours to stabilize after initial servicing with agent and lengthy equilibration times are required for each adjustment of vapor concentration. This apparatus uses a regular house line for compressed air and nitrogen, which generally results in air mixture having a very low relative humidity and consequently only gives a limited, and sometimes false, indication of the performance of the detector being tested.

The portable agent generator described in U.S. Pat. No. 4,069,701 to Frederick C. Baldauf and Kwok Y. Ong, issued Jan. 24, 1978, provides a readily transportable generator which succeeded in providing a low, constant vapor of test agent at rapid equilibration times and with a concentration of agent directly related to air flow rate. This generator, however, is also limited to only the use of existing climatic conditions which vary from day to day, and therefore resulted in varying evaluations of the detector being tested.

Subsequent to the development of the above portable agent generator, applicants were the first to recognize that many detector items, such as the point source agent alarm (i.e., the Army M256 Ionization Dectector Kit), perform differently under different climatic conditions and are particularly sensitive to changes in relative humidity of the operating environment. The phenomenon of relative humidity effects upon the operation of toxic agent vapor and aerosol detectors was not previously appreciated in the art prior to applicants' invention since there was no existing system for rapidly generating a reliable and stable concentration of agent vapor under varying relative humidity conditions.

The present invention was conceived and reduced to practice to provide a complete system which would simultaneously provide a very reliable and stable concentration of chemical agent vapor or aerosol and simulate various relative humidity conditions. The present system can also produce variable temperature control for a range of agent concentration generation and will allow for testing of detectors by means of either static or dynamic exposure to the test agent vapor and aerosol.

SUMMARY OF THE INVENTION

A method and system for generating chemical agent vapors and aerosols of uniform concentration under variable, controlled relative humidity and temperature conditions for testing reliability of agent detectors comprising the steps of providing a regulated flow of pressurized air to an agent reservoir selected from the group consisting of an agent bubbler and an agent nebulizer to generate an agent laden air stream, concurrently providing a regulated flow of pressurized air though two parallel flowmeters to a water bubbler and a drierite column to obtain, respectively, a 100 percent relative humidity air stream and a 0 percent relative humidity air stream; combining said 100 percent and 0 percent relative humidity air streams in a desired ratio to give a resultant air stream having a desired relative humidity, as measured by a wet and dry bulb hygrometer; for use in diluting said agent laden air stream, combining the diluting air stream and the agent laden air stream and introducing the combined agent laden air stream into a mixing and testing chamber to give a dilute agent laden air having a controlled relative humidity; exposing agent detectors to the dilute agent laden air within the chamber to test detector performance; and exhausting excess air flow from said chamber through a charcoal filter by means of a vacuum system. A bubbler is used as the agent reservoir for producing an agent vapor and a nebulizer is used for generating an air stream containing an agent aerosol. A controlled supply of nitrogen gas can be introduced into the agent reservoir means for generating an agent vapor.

The principal object of this invention is to provide an agent generation system and method for calibrating and testing the agent sensitivity of agent detector alarm system under varying conditions of relative humidity and temperature.

Another object of this invention is to provide an agent dilution system which will give a controlled concentration of agent vapor or agent aerosol under various controlled conditions of relative humidity and temperature.

A further object of this invention is to provide a multi-purpose chemical agent generation system which has interchangeable agent test chambers to avoid inter-agent contamination.

A still further object of this invention is to provide an agent generation system having a test chamber which allows exposure of a detector item from within the chamber or from outside the chamber by means of a sample port.

An additional object of this invention is to provide an agent generation system which will allow testing of an agent detector alarm by either static or dynamic exposure to agent laden air.

Other objects and advantages of the invention will become apparent from the following detailed description of the invention.

The drawing is a schematic flow diamgram of the agent generation system of the invention.

The free standing generation system of this invention is comprised of a source of pressurized air consisting of an intake filter canister 2 through which air flows through an oilless air compressor 3 to provide a pressurized air flow to the system which is regulated by pressure relief valve 4 and monitored by gage 5. The flow of pressurized air to the agent introduction chamber (reservoir), e.g., agent bubbler 9 is regulated by a high accuracy needle valve in flowmeter 8 through in-line restrictive orifice 6, which limits the flow of air passing through drierite column 7. As an alternative to flowing compressed air through orifice 6 and drierite column 7, a controlled source of $N_2$ could be directly introduced into the agent reservoir 9 through the needle valve in flowmeter 8. The agent reservoir 9 is maintained at a desired temperature through use of a temperature bath 20 with associated heating and cooling means, not shown.

Pressurized air is concurrently introduced, in parallel, to a humidifying bubbler 12 and a large capacity drierite column 13 by means of needle valves in flowmeter 10 and 11, respectively, to provide air streams of controlled relatively humidity for subsequent use in diluting the agent laden air from bubbler 9. The air stream from humidifying bubbler 12, containing 100 percent relative humidity air and the air stream from drierite column 13, containing zero percent relative humidity air, are combined to give a resulting air stream for dilution with a controlled relatively humidity dependent upon the flow rates of the respective fed streams. The relative humidity of the resultant air stream is measured by a wet and dry bulb hygrometer 14 before it is combined with the agent-laden air stream from the output of agent reservoir 9 to obtain a desired concentration of either chemical vapor or aerosol under a controlled relative humidity condition. This combined stream is introduced into a mixing and testing chamber 15, which is a container in the form of a box or tube, from which samples of dilute agent laden air can be withdrawn through a conventional sample port 19 or into which test items may be placed for exposure to the agent. The chamber 13 may be optionally equipped with a motor driven waiver arm assembly 16 which is attached to the chamber 15 with the waiver arm extending into the test chamber as shown in the FIGURE. This waiver arm has mounting means, e.g., a clip (not shown) for attachment of a test item for movement of the test item through the agent laden air within the chamber and thus allows dynamic testing of the sampling feature of conventional point source agent detector systems, e.g., M236 detector tickets. Under normal operations, external environmental temperature dictates the generator temperature, but a controlled air temperature may be incorporated as desired through use of conventional temperature controllers, not shown. Excess air flow is exhausted from the mixing chamber 15 through a charcoal filter canister 17 by means of a conventional vacuum system, such as vacuum pump 18. The combined effects of pressure and vacuum and the use of the one way flopper valves 21 (vacuum release safety valve) and 22 (pressure release safety valve), maintain a zero pressure differential at the sample port 19 of chamber 15. Though this zero pressure differential feature is critical only for aerosol generation, it provides added safety during vapor generation in releasing pressure or vacuum in the event of a component failure, i.e., vacuum pump failure and the like.

The agent generator, as shown in the drawing, operates from regulated, pressurized air supplied by a small oilless air pump compressor 3, e.g., 100 V. AC. Air flows are monitored with high quality needle valves. The air flow towards the agent reservoir 9 through restrictive orifice 6 and drierite column 7 is controlled with a high accuracy needle valve in flowmeter 8. The agent reservoir 9, which can be a conventional bubbler for producing agent vapor or a conventional nebulizer for producing agent aerosol, is immersed in a temperature controlled bath 20 having a sensitive temperature controlled and associated means for cooling and heating the bath. The temperature of the bath significantly effects the stability of the generator concentration. The air for dilution of the agent vapor is the sum total of the zero percent relative humidity air flowing through the large drierite column 13 by means of the needle valve in flowmeter 11 and the 100 percent relative humidity air that flows through humidifying water bubbler 12 by means of the needle valve in flowmeter 10. The dilution air stream from the combined streams from bubbler 12 and drierite column 13 will have a regulated relative humidity, dependent upon the respective flow rates of the making streams, as measured by wet and dry bulb hygrometers 14. Alternative methods of determining relative humidity of the dilution stream could obviously be used in place of the hygrometer 14. The measurement could be eliminated entirely once the generator has been calibrated over a range of relative humidities. The moisture laden dilution air stream is then combined with the agent-laden air from the output of agent reservoir 9 to obtain a desired concentration of toxic chemical vapor/aerosol under controlled relative humidity conditions. The resultant stream is then introduced into a mixing and testing chamber 15, either in the form of a box or tube, which can optionally be equipped to give a controlled air temperature. In the absence of temperature controls, the generator temperature would be dependent upon the external environmental temperature. Agent detector items can be tested alternatively by being placed within the chamber 15 for exposure to the agent vapor or by exposure to a sample of the dilute agent vapor withdrawn from the chamber by means of sample port 19. The chamber 15 can optionally be equipped with a motorized waving arm 16 to allow dynamic sampling by the detector kits to be tested and to stir the cloud of agent within the chamber. Ordinarily, however, the amount of air flow through the chamber is sufficient for self mixing. The excess air flow in the chamber 15 is removed through a charcoal type canister 17 by means of a vacuum pump 18 or equivalent vacuum system. The combined effects of pressure and vacuum with the aid of conventional one way flapper valves, not shown, maintains a zero pressure differential at the sample port 19.

Following step by step operational procedures, the agent reservoir bath is adjusted to the desired temperature by means of a sensitive temperature controller and associated conventional heating and cooling means to insure a stable generator concentration. An adequate supply of indicating drierite in drying columns 7 and 13 and an adequate level of water in water bubbler 12 must be maintained prior to start-up of the generator. Following inspection of all connections for leaks or obstructions, the pressure relief valve 4 and the valve on vacuum pump 18 are opened. The generator pump 3 is then turned on, with the agent reservoir 9 disconnected from the agent mixing chamber 15. Flowmeter 10 to the water bubbler 12, flowmeter 11 to the drierite column 13 and pressure relief valve 4 are then adjusted to obtain a desired total air flow rate and percent relative humidity while maintaining a 2-3 psig reading on pressure gage 5. A water manometer is then attached to the sample port 19 and the vacuum valve is adjusted to obtain a very slight negative pressure within the generator system. The generator pump 3 is then turned off before the input of agent reservoir 9 (either a bubbler or nebulizer type) is connected to the air line from flowmeter 8. Once the agent reservoir is attached to the generator system, the generator motor 3 is restarted and flowmeter 8 is adjusted to the required setting for desired agent vapor concentration. The internal pressure of the generator is then balanced by readjustment of the vacuum valve. Finally, the water manometer is removed from the sample port and the sample port is closed. The generator is now in operation, however, best results are obtained when the generator is allowed to equilibrate for approximately 15-30 minutes to insure temperature stability.

The operation of the agent vapor dilution apparatus can be adjusted to increase or decrease agent concentration by performing one or more of the following steps:

(1) Increasing or decreasing the air flow rate through flowmeter 8 to the agent reservoir 9 will respectively increase or decrease the concentration of agent in the resulting agent vapor/aerosol;

(2) Increasing or decreasing the total flow rate of air of dilution through flowmeter 10 to water bubbler 12 and flowmeter 11 to drierite column 13 will respectively decrease or increase agent concentration;

(3) Increasing the concentration of agent within the agent reservoir will obviously increase the concentration range of agent vapor/aerosol generated and (4) Increasing the temperature of the agent reservoir bath 20 will increase the concentration of agent in the generated vapor/aerosol provided that the temperature does not exceed the temperature at which the particular agent will decompose or deteriorate.

Examples of Agents Tested Over 5-95% RH Conditions + Temperature, etc.

In the preferred method of operation, the air flow to the agent reservoir is limited, as a safety factor to 300 ml/min by the restrictive orifice 6 and flowmeter 7. The air flow is passed through 10 ml of 1% GB (isopropyl methyl phosphonofluoridate) solution (in propylene glycol) within the agent reservoir 9, e.g., bubbler. The temperature of the GB is maintained constant at the desired temperature by temperature controller in bath 20, e.g., at 0° C. The agent vapor eluted from the reservoir is diluted with a large amount of air from the combined dilution streams from bubbler 12 and drierite column 13 to produce a diluted vapor of approximately 1.0 mg/liter under controlled relative humidity conditions within the desired range of 5-95%.

The actual control of relative humidity, using minimum amounts of dilution, is shown for the following typical examples:

(1) For a desired 50% relative humidity, the flowmeters 10 and 11 (Matheson Model 604 tube) are each adjusted to a glass float setting of 7, which corresponds to a flow of 4 liter/min. of air, thus giving a total flow of 8 liter/min. of 50% RH;

(2) For low relative humidity in the range of 0-5%, the wet side flow is cut off and the flow through the drierite side is set to equal 8 liter/min. The agent concentration is not disturbed. Similarly, relative humidity of 95-100% is achieved by cutting off flow through the drierite side and setting the flow through bubbler 12 at 8 liter/min.

(3) Outside of the above ranges of relative humidity, the percent relative humidity is estimated by using the formula $$[AF_W/(AF_W + AF_D)] \times 100\% = \% \text{ Relative Humidity}$$

with $AF_W + AF_D$ being fixed at 8 liter/min. in our tests, thus giving the desired relative humidity (RH) with the $AF_W$ from the formula $$AF_W = RH\% \text{ (8 liter/min.)}$$

Where 30% relative humidity is desired, a wet air flow ($AF_W$) of 2.4 liter/min. is required. A flowmeter setting of 4.2 represents a $AF_W$ of 2.4 liter/min. and the dry side is set to equal 5.6 liter/min., which is corresponding to a setting of 9.7. Thus by selecting the same final flow through the system, the agent concentration will remain stable.

Different agent concentrations are obtained by varying flow rates through the agent reservoir 9 and by adjusting the initial concentration of agent solution charged to the agent reservoir.

Thus by keeping the final volume of air and consequently the ratio of agent to vapor volume constant, measurements of detector capability can be made over the entire range of relative humidity. Similarly, the apparatus can, through use of a fixed ratio of dilution stream to agent, will maintain the same % relative humidity over a range of varying temperatures, wherein the temperature is regulated through means of either regulating the temperature of the agent reservoir through bath 20 or by means of regulating the temperature of the air entering the system.

The generation of this invention can be used to prepare dilute vapor or aerosols of toxic agents such as HD (mustard) VX (aerosol) and industrial chemical vapors/aerosols, such as controlled concentration of the environmental air pollutants nitric oxide, $SO_2$, alcohols, ethers, gasoline, diesel fumes, which are conventionally monitored at industrial sites and environmental monitoring stations. Similarly, the generator and method of this invention can be used in conjunction with other sources of air supply, i.e., house air lines or compressed air tanks, as well as other carrier gases, e.g., nitrogen. Thus, by way of illustration, the orifice 6, and drierite column 7 could be eliminated if the carrier air from compressor 3 is replaced by a separate source of controlled N$_2$ for use as a carrier gas in agent reservoir 9.

The details of the method of construction of the generator including the size and shape of the unit do not form a critical feature of this invention and can be varied within the scope of the invention. The pressure valves, flowmeters, air pump, orifices, bubbler, nebulizer, hygrometers, drierite column, and the like are conventional, commercially available units which can be varied within the skill of one in the art. As mentioned previously, the hygrometer used to measure the relative humidity of the air of dilution can be eliminated from the generating system once the generator has been calibrated over a range of percent relative humidity, since the percent relative humidity of the dilution air can thereafter be accurately determined by the following formula:

$$\%RH = [AF_W/(AF_W + AF_D)] \times K \times 100\%$$

wherein
$AF_W$ = air flow through the H$_2$O bubbler
$AF_D$ = air flow through the drierite column
K = calibrated efficiency factor (normally within the range of 0.9 to 1.0) which is in turn determined as to
K = (% relative humidity observed)/(% relative humidity calculated)
assuming 100% efficiency.

The essential features of the generator and method of this invention is the generation of a low, stable concentration of agent vapor/aerosol under variable and controlled condition of relative humidity and temperature within relatively rapid equilibration times, i.e., within a few minutes.

It is obvious that other modifications can be made in the invention by one skilled in the art. Applicants therefore wish to be limited only by the scope of the appended claims.

We claim:

1. A system for generating a stable concentration of agent vapors and aerosols under variable controlled conditions of relative humidity and temperature for testing agent detector systems comprising:
   means for providing a regulated, pressurized air flow to an agent generator reservoir means;
   an agent generator reservoir means containing a dilute liquid agent solution through which air is passed to produce an agent-laden air stream;
   temperature control means for maintaining a desired constant temperature of liquid agent solution within the reservoir means;
   interconnected means for adding a regulated flow of air having a controlled relative humidity to produce a dilute agent-laden air having controlled conditions of relative humidity and temperature;
   a combination mixing and testing chamber means for mixing the resulting dilute agent-laden air and providing dynamic exposure of an agent detector system disposed within said chamber to said agent; and
   associated exhaust means for removing excess agent-laden air from said system.

2. The system of claim 1 wherein aid interconnecting means for providing regulated flow of air having a controlled relative humidity comprises:
   parallel means for providing a regulated flow of pressurized air to a water bubbler and a drierite packed column, respectively;
   a bubbler containing water through which air is passed to produce a saturated air stream of 100% relative humidity;
   a drierite packed column through which air is passed to produce an air stream of 0% relative humidity; and
   interconnecting means for combining said air stream of 100% and 0% relative humidity to give a regulated air flow of controlled relative humidity for addition to the agent-laden air.

3. The system of claim 2 wherein the agent reservoir means is a bubbler means for producing an agent vapor.

4. The system of claim 2 wherein the agent reservoir means is a nebulizer means for providing an agent aerosol.

5. The system of claim 2 wherein the means for providing air of controlled relative humidity includes a wet and dry bulb hygrometer.

6. The system of claim 2 wherein the system includes means to maintain the system under a slight positive pressure and the exhaust system consists essentially of a charcoal filter and a vacuum system for preventing the exhaust of toxic agents to the atmosphere.

7. The system of claim 2 wherein the mixing and testing chamber have a sample port for extracting a sample of agent-laden air for use in testing a point source agent alarm.

8. The system of claim 7 wherein the mixing and testing chamber have an associated motor driven waiver arm having means thereon for attaching an agent alarm system for dynamic exposure of said alarm to the agent within said chamber.

9. The system of claim 2 further including means for concurrently supplying a source of pressurized air to both the agent reservoir means and the bubbler and drierite column for supplying air of controlled relative humidity.

10. The system of claim 2 wherein a regulated pressurized flow nitrogen is provided to the agent reservoir means to produce an agent-laden nitrogen gas.

11. A method for generating a stable concentration of agent vapors and aerosols under variable controlled conditions of relative humidity and temperature for testing agent detector system comprising:
   steps of generating an agent-laden air stream at a controlled constant temperature by passing a regulated, pressurized air stream through an agent reservoir means containing dilute liquid agent solution at a controlled constant temperature;
   contemporaneously providing a regulated flow of air under controlled condition of relative humidity and temperature;
   combining said agent-laden air stream with the regulated flow of air having a controlled relative humidity and temperature to produce a dilute agent-laden air stream of controlled relative humidity and temperature, exposing an agent detector system to the resulting dilute agent-laden air stream to test the performance of said detector; and
   exhausting excess agent-laden air to the atmosphere.

12. The method of claim 11 wherein air of controlled conditions of relative humidity and temperature is provided by proportionately combining an air stream of 100% relative humidity and an air stream of 0% relative humidity to produce an air stream having a desired relative humidity.

13. The method of claim 12 wherein the air stream of 100% relative humidity and 0% relative humidity are obtained by passing a regulated flow of air through a water bubbler and a drierite packed column, respectively.

14. The method of claim 13 wherein a single source of air is used to provide concurrent air flow to the agent reservoir, the water bubbler and the drierite packed column.

15. The method of claim 12 wherein the agent reservoir means is an agent bubbler and the resulting generated air stream contains an agent vapor.

16. The method of claim 12 wherein the agemt reservoir means is an agent nebulizer and the resulting generated air stream contains an agent aerosol.

17. The method of claim 11 wherein the agent is a toxic agent and the method is performed under vacuum with excess agent being passed through a charcoal filter to prevent exhaust of toxic and pollutant agents to the atmosphere.

18. The method of claim 17 wherein the agent is selected from the group consisting of toxic nerve agents, gasoline, and industrial air pollutants.

19. The method of claim 18 wherein the agent is a GB toxic nerve agent vapor.

20. The method of claim 18 wherein the agent is a VX toxic nerve agent aerosol.

21. The method of claim 11 further including the step of providing dynamic exposure of the agent detector system by means of attaching the detector to a motor driven waiver arm which is positioned to move the detector through the dilute agent-laden air stream.

22. The method of claim 11 wherein the agent detector system is exposed to the dilute agent-laden air.

23. The method of claim 11 wherein a regulated flow of nitrogen gas is provided to the agent reservoir to produce an agent-laden nitrogen gas stream.

* * * * *